United States Patent [19]  
Arcamone et al.

[11] 4,025,623  
[45] May 24, 1977

[54] 4'-EPI-6'-HYDROXYADRIAMYCIN AND METHOD OF USE

[75] Inventors: Federico Arcamone, Nerviano (Milan); Alberto Bargiotti, Milan; Giuseppe Cassinelli, Voghera (Pavia); Aurelio diMarco, Milan, all of Italy

[73] Assignee: Societa' Farmaceutici Italia S.p.A., Milan, Italy

[22] Filed: Oct. 10, 1975

[21] Appl. No.: 621,582

[30] Foreign Application Priority Data

Oct. 29, 1974 United Kingdom ............ 46644/74

[52] U.S. Cl. .................................. 424/180; 536/4; 536/17; 536/18
[51] Int. Cl.² .......................................... A61K 31/71
[58] Field of Search .... 260/210 AB, 210 R, 211 R; 424/180; 536/4, 18, 17

[56] References Cited

UNITED STATES PATENTS 3,784,541  1/1974  Culbertson et al. ......... 260/210 AB
3,803,124  4/1974  Arcamone et al. ......... 260/210 AB

OTHER PUBLICATIONS

Pigman "The Carbohydrates," Academic Press Inc., New York, N.Y., pp. 208–213.

*Primary Examiner*—Johnnie R. Brown
*Attorney, Agent, or Firm*—Hubbell, Cohen, Stiefel & Gross

[57] ABSTRACT

The novel glycoside antibiotic: 4'-epi-6'-hydroxydaunomycin is prepared by condensing daunomycin with a novel protected, reactive derivative, which is 1,2,3-trideoxy-4,6-di-O-(p-nitrobenzoyl)-3-trifluoroacetamido-L-arabino-hex-1-enepyranose and thereafter removing the protecting groups. A further novel glycoside antibiotic: 4'-epi-6'-hydroxyadriamycin is prepared by reacting 4'-epi-6'-hydroxydaunomycin with bromine to form an intermediate bromo derivative which is then mildly hydrolyzed to form 4'-epi-6'-hydroxyadriamycin. These novel glycoside antibiotics, while not as effective as the parent compounds daunomycin and adriamycin in the treatment of tumors, are considerably less toxic than the parent compounds.

10 Claims, No Drawings

4'-EPI-6'-HYDROXYADRIAMYCIN AND METHOD OF USE

CROSS REFERENCE TO RELATED APPLICATIONS

This application is related to and incorporates by reference the contents of copending applications Nos. 560,104, 560,105 and 568,437, filed respectively on Mar. 19, 1975, Mar. 19, 1975 and Apr. 16, 1975, said applications being owned by the assignee hereof.

BACKGROUND OF THE INVENTION

1. Field of the Invention

The present invention relates to anthracyclinone glycoside antibiotics and processes for the preparation thereof. More particularly, the invention relates to the novel antibiotics, 4'-epi-6'-hydroxydaunomycin and 4'-epi-6'-hydroxyadriamycin. The invention also relates to certain novel intermediates used in the preparation of these antibiotics.

2. The Prior Art

Glycoside antibiotics are, of course, known. For example, daunomycin and its aglycone, daunomycinone are known compounds. They are described and claimed in British Pat. No. 1,003,383. Adriamycin and its aglycone, adriamycinone are also known compounds, known described and claimed in British Pat. No. 1,161,278; both such British patents being owned by the assignee hereof.

The above glycoside antibiotics are prepared according to the processes disclosed in application Ser. Nos. 560,104 and 560,105, incorporated herein by reference, by reacting the aglycone, or a reactive derivative thereof with a reactive protected derivative of the pyranose sugars daunosamine and 4'-epidaunosamine.

Application Ser. No. 568,437 describes a process for producing derivatives of daunomycin and adriamycin, which process utilizes a novel, reactive, protected derivative of a 1,2-unsaturated pyranoid sugar. These pyranoid sugars are known generically as "glycals". See, for example, the monograph entitled "Unsaturated Sugar, Advance in Carbohydrate Chemistry", Vol. 20, page 67 (1965, Academic Press, London). In this monograph a number of glycals including D-arabinal (3,4-di-O-acetyl); L-arabinal (3,4-di-O-acetyl); D-allal (4,6-O-benylidene); D-glucal (4-deoxyl; L-glucal (3,4di-O-acetyl), etc., are described.

The process of the present invention also utilizes a novel, reactive, protected derivative of a 1,2-unsaturated pyranoid sugar, the latter being obtained from L-glucose according to techniques which are described in part in the literature, see, e.g. G. N. Bollenback; Methods in Carbohydrate Chemistry II, 326, 1963; L. F. Wiggins; ibid, II, 188, 1963 and A. C. Richardson; Carbohydrate Research, 4, 422, (1967).

SUMMARY OF THE INVENTION

This invention relates to the novel antitumor glycoside antibiotics 4'-epi-6'-hydroxydaunomycin and 4'-epi-6'-hydroxyadriamycin as well as to new processes for preparing them. These processes involve the preparation and use of certain novel intermediates which are also within the ambit of the invention.

The new glycoside antibiotics of the invention possess antimitotic activity both in vivo and in vitro and they are useful therapeutic agents for the treatment of tumors and viral diseases in humans, such as Solid Sarcoma 180 and $L_{1210}$ leukemia.

The glycoside antibiotics of the invention have the general formula:

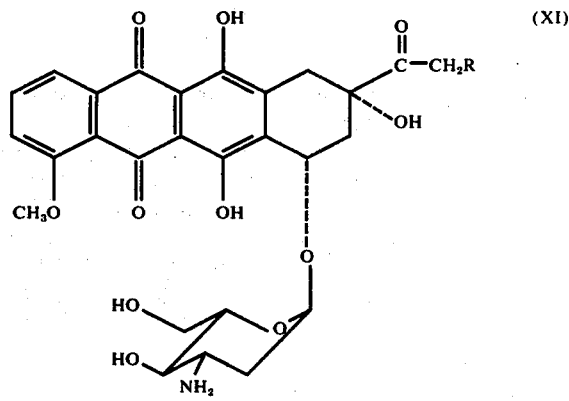

wherein R is H or OH. Also included within the scope of the invention are the hydrochloride salts thereof.

More specifically, the invention provides a process which is used for preparing 4'-epi-6'-hydroxydaunomycin (I)

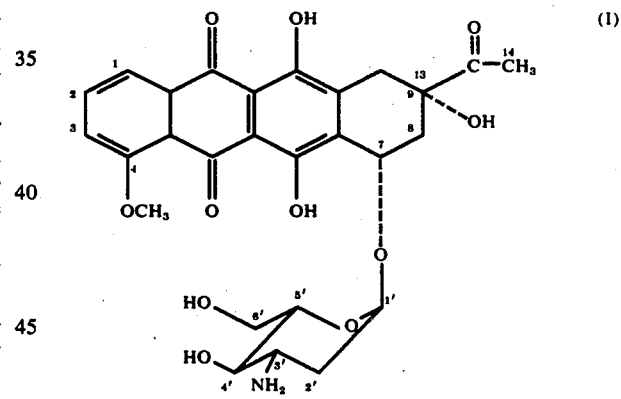

by condensing daunomycinone (II), in the presence of an acid catalyst, such as p-toluene sulfonic acid,

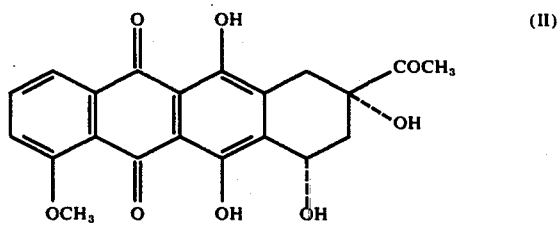

with a novel reactive, protected 1,2-pyranoid sugar derivative which also forms part of the invention, namely, 1,2,3-trideoxy-4,6-di-O-(p-nitrobenzoyl)-3-trifluoroacetamido -L-arabino-hex-1-enepyranose (III)

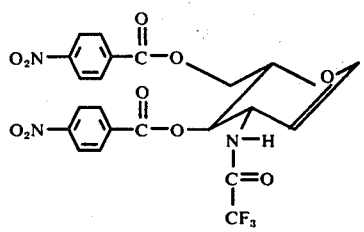

to form a glycosidic linkage between the daunomycinone and the 1,2-pyranoid sugar. After the acid catalyzed condensation reaction, the protecting groups on the sugar moiety are removed to produce the biologically active compound (I), which is isolated in the form of the hydrochloride. It is important to note that under the reaction conditions of the present process, substantially only the α glycoside is formed; the β anomer being present in only very small amounts in the reaction mixture.

In order to obtain 4'-epi-6'-hydroxyadriamycin (V), compound (I) is treated with a solution of bromine in chloroform to first produce 14-bromo-4'-epi-6'-hydroxydaunomycin (IV),

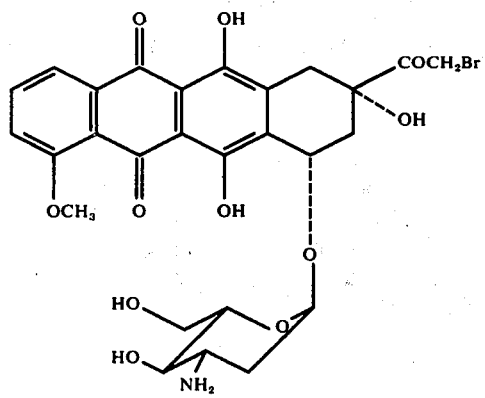

Controlled hydrolysis of compound (IV) with sodium formiate yields 4'-epi-6'-hydroxyadriamycin (V),

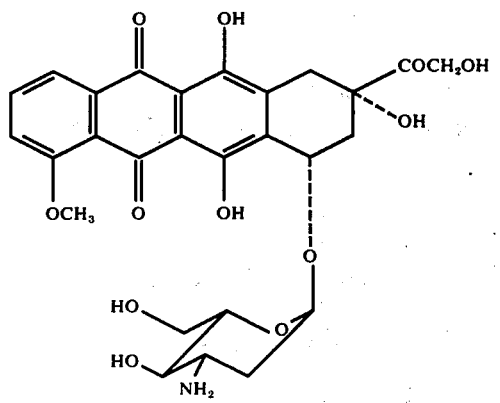

which is also isolated in the form of the hydrochloride. The reactive, protected sugar compound (III) which is condensed with daunomycinone (II) is itself a novel intermediate which is obtained from the likewise novel compound, 3-amino-2,3-dideoxy-L-arabino-hexose (VI),

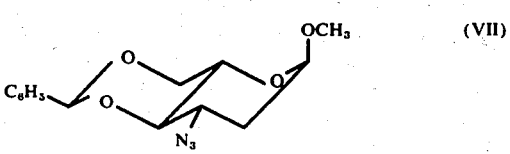

The amino-sugar VI was previously unknown in the L-series and has now been obtained by us for the first time according to the following procedure. L-glucose is converted to methyl-3-azido-4,6,-O-benzylidene-2,3-dideoxy-alpha-L-arabino-hexopyrano-side (VII)

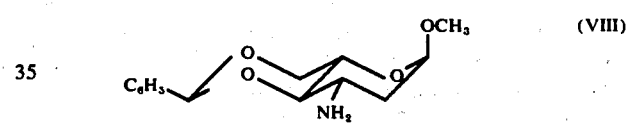

according to known procedures for the D-isomer (G. N. Bollenback, "Methods in Carbohydrate Chemistry" II, 326, 1963. Acad. Press. L. F. Wiggins, ibid, II, 188, 1963. A. C. Richardson, Carbohydrate Research, 4, 422, (1967)). This compound (VII) is then converted, by catalytic hydrogenation at 60 p.s.i. at room temperature in the presence of Raney nickel to the 3-amino derivative (VIII),

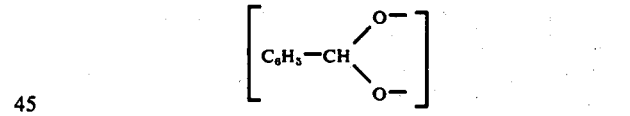

After removal of the benzylidene moiety $$\left[ C_6H_5-CH \begin{array}{c} O- \\ \\ O- \end{array} \right]$$

by hydrolysis with methanolic hydrogen chloride, methyl-3-amino-2,3-dideoxy-alpha-L-arabino-hexopyranoside (IX), is obtained.

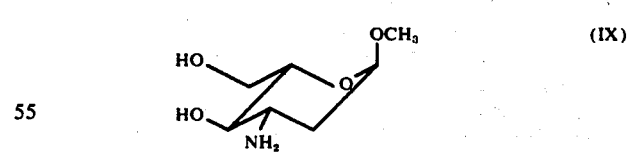

This compound (IX) (which is also heretofore unknown in the D-series) is then converted by acid treatment with refluxing 1 N hydrochloric acid for 5 hours into compound (VI) which is isolated in the form of the hydrochloride.

Compound (VI) is then reacted with trifluoroacetic anhydride, followed by treatment with a lower aliphatic alcohol such as methyl, ethyl or isopropyl alcohol to form the N-trifluoroacetyl protected derivative (X),

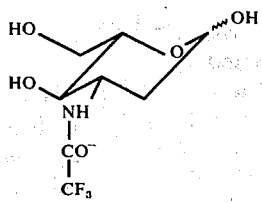

which is finally reacted with p-nitrobenzoyl chloride in pyridine, followed by a mild alkaline treatment, in order to obtain 1,2,3-trideoxy-4,6-O-(p-nitrobenzoyl)-3-trifluoroacetamido-L-arabino-hex-1-enepyranose (III) in good yield.

DESCRIPTION OF THE PREFERRED EMBODIMENTS

The following examples are given to more fully describe the preparation of the novel compounds of the invention without, however, being a limitation thereof.

EXAMPLE 1

Preparation of the novel intermediate: 1,2,3-trideoxy-4,6-di-O-(p-nitrobenzoyl)-3-trifluoroacetamido-L-arabino-hex-1-enepyranose (III)

A. 2.85 g. of methyl-3-azido-4,6-O-benzylidene-2,3-dideoxy-α-L-arabino-hexopyranoside (VII) obtained from L-glucose according to the techniques described in the literature, were dissolved in 40 ml. of anhydrous methanol and hydrogenated at 60 p.s.i. at room temperature in the presence of Raney nickel for 3 hours. The catalyst was filtered off and the filtrate evaporated in vacuo to a residue.

The residue was crystallized from ethyl acetate to give 2.17 g. of methyl-3-amino-4,6-O-benzylidene-2,3-dideoxy-α-L-arabino-hexopyranoside (VIII).

M.P. 95°–96° C.; $[\alpha]_D^{20°} = -86°$ ($c = 0.5$ CHCl$_3$). Yield 84%; Compound (VIII) was characterized by NMR and mass spectroscopy as follows: N.M.R. (CDCl$_3$): 1.3–2.3δ ($m$, 2H, C(2)H$_2$), 1.4δ (broad $s$, 2H, NH$_2$), 3.2–4.4δ(multiplets, 5H, C(3)H, C(4)H, C(5)H, C(6)H$_2$), 3.37δ ($s$, 3H, CH$_3$O), 4.76δ ($dd$, J=3.5 H$_2$ and J< 1Hz, 1H, C(1)H), 5.57δ ($s$, 1H),

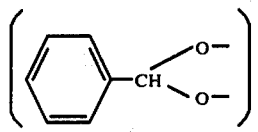

7.2–7.7δ ($m$, 5H, C$_6$H$_5$).

MS (DIS): $m/e$ 265 (M$^+$), $m/e$ 234 (M—OCH$_3$), $m/e$ 162

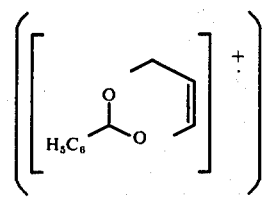

$m/e$ 149 (C$_6$H$_5$—CH=O$^+$=CH$_2$—CHO) $m/e$ 105 (C$_6$H$_5$—CO$^+$).

B. 2.15 g. of compound (VIII) were dissolved in 40 ml. of 0.5N methanolic hydrogen chloride and the mixture was stirred at room temperature for one hour. The solution was evaporated to half volume, anhydrous ether was added and the resulting crystals were collected by suction and washed with a small amount of anhydrous ether to obtain 1.5 g. of methyl-3-amino-2,3-dideoxy-α-L-arabion-hexopyranoside (IX), m.p. 120° C. dec.; $[\alpha]_D^{20°} = -92°$ ($c = 0.4$ H$_2$O). Yield 87%. N.M.R. (D$_2$O) = 1.5–2.5δ ($m$, 2H, C(2)H$_2$), 3.2–4.0δ (multiplets, 5H, C(3)H, C(4)H, C(5)H, C(6)H$_2$), 3.41δ ($s$, 3H, CH$_3$O—), 4.98δ ($dd$, J, = 3Hz and J = 1.5 Hz, 1H, C(1)H).

MS (DIS): $m/e$ 178 (M+1), $m/e$ 146 (M-31), $m/e$ 86 (H$_2$N$^+$=$^3$CH-$^2$CH=$^1$CH-OCH$_3$), $m/e$ 72 (H$_2$N$^+$=CH—CH$_2$—CHO), $m/e$ 59 (H$_2$N$^+$=CH—CH—OH), $m/e$ 44

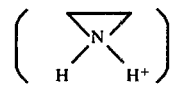

C. 1.5 g. of the amino-glycoside (IX) were refluxed in 1N hydrochloric acid for 5 hours. The solution was then shaken at room temperature with Amberlite IR 45 (OH$^-$) resin until the pH of the solution reached 5. The resin was filtered off and the filtrate evaporated in vacuo to one half volume and then freeze-dried. The residue was crystallized from methanol-ethyl acetate to give 1.33 g. of 3-amino-2,3-dideoxy-L-arabino-hexose (VI) as the hydrochloride; m.p. 155°–157° C. dec. $[\alpha]_D^{20} = -55°$ ($c = 0.5$ H$_2$O). Yield 95%. N.M.R. (D$_2$O): 1.7–2.7δ ($m$, 2H, C(2)H$_2$), 3.3–4.1δ (multiplets, 5H, C(3)H, C(4)H, C(5)H, C(6)H$_2$), 5.06δ ($dd$, J = 10 Hz and J = 2Hz, 0.4H, C(1)H$_{ax}$), 5.46δ (broad $s$, W$_{1/2}$ H = 7 Hz, 0.6 H, C(1)H$_{eq}$).

D. To a suspension of 1.25 g. of compound (VI) in anhydrous ether, there were added 7.6 ml. of trifluoroacetic anhydride with cooling and stirring. The mixture was stirred at room temperature for 20 hours and the resulting clear solution was evaporated in vacuo. The resulting solid residue was dissolved in 120 ml. of anhydrous methanol and kept at room temperature for 20 hours. After removing the solvent, the residue was crystallized from acetone-chloroform to give 1.72 g. of 2,3-dideoxy-3-trifluoroactamido-L-arabino-hexose (X); m.p. 177° C., $[\alpha]_D^{20} = -58°$ ($c = 0.5$ dioxane). Yield 90%.

Mass spectrum: $m/e$ 242 (M—OH), $m/e$ 169

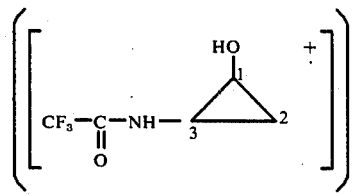

$m/e$ 155 (HO—CH—CH=NH—COCF$_3$), $m/e$ 140

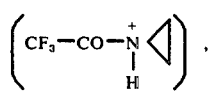

$m/e$ 114 (CF$_3$—CO—N$^+$H$_3$).

E. 1.1 g. of compound (X) were added in small portions, over a 30 ml. of anhydrous pyridine and stirring was continued at room temperature for 20 hours. To the solution, cooled to 0° C., an ice-cooled solution of 1.44 g. of sodium bicarbonate in 20 ml. of water was added and the mixture was finally poured into 350 ml. of ice water.

The precipitate was removed by filtration, washed with water and dried over phosphorous pentoxide. The dry product was finally crystallized from dichloromethane-ether to give 2.3 g. of 1,2,3-trideoxy-4,6-di-O-(p-nitrobenzoyl)-3-trifluoroacetamido-L-arabino-hex-1-enepyranose (III), m.p. 214°–215° C., $[\alpha]_D^{20} = -117°$ ($c = 0.5$ CHCl$_3$); Yield 95%. N.M.R. (CDCl$_3$ — DMSO —d$_6$ 3:1): 4.3–5.6$\delta$ (multiplets, 4H, C(3)H, C(4)H, C(5)H, C(2)H, 4.52$\delta$ (broad s, W$_{1/2}$H, 2H, C(6)H$_2$), 6.57$\delta$ (broad s, W$_{1/2}$H = 5Hz, 1H, C(1)H), 8.21$\delta$ (s, 4H aromatic), 8.35$\delta$ (s, 4H aromatic), 9.27$\delta$ (s, 4H aromatic), 9.27$\delta$ (s, 1H, NH).

EXAMPLE 2

Preparation of 4'-epi-6'-hydroxydaunomycin (I)

200 mg. of daunomycinone (II) were dissolved in 100 ml. of anhydrous benzene and to the resulting solution there were added 540 mg. of 1,2,3-trideoxy-4,6-di-O-(p-nitrobenzoyl)-3-trifluoroacetamido-L-arabino-hex-1-enepyranose (III) and 20 mg. of p-toluenesulfonic acid.

The reaction mixture was stirred at 55° C. for 20 hours and after cooling to room temperature the formed precipitate was filtered and crystallized from ethanol to give 340 mg. of the protected 7-O-[4',6'-di-O-(p-nitrobenzoyl)-3'-trifluoroacetamido-α-L-arabino]-daunomycinone; m.p. 282° C., $[\alpha]_D^{20} = +260° +5°$ ($c = 0.05$ CHCl$_3$).

The thusly obtained protected glycoside was then dissolved in 20 ml. of dioxane and, after cooling to 0° C., was treated with 0.2 N aqueous sodium hydroxide. After one hour at 0° C., the pH of the solution was adjusted to 4.5 with 1N hydrochloric acid and the dioxane was remoed by evaporation in vacuo. The resulting aqueous solution, after washing with chloroform, was adjusted to pH 8.5 with 0.2 N aqueous sodium hydroxide and then extracted with chloroform.

The extract was dried over anhydrous sodium sulphate and concentrated to a small volume.

One equivalent of methanolic hydrogen chloride was added to obtain 160 mg. (56% yield) of 4'-epi-6'-hydroxydaunomycin as the hydrochloride, m.p. 199°–201° C., $[\alpha]_D^{20} = +388° + 5°$ ($c = 0.05$ CH$_3$OH).

EXAMPLE 3

Preparation of 4'-epi-6'-hydroxyadriamycin (V)

0.25 g. of 4'-epi-6'-hydroxydaunomycin (I) was dissolved in a mixture of 3.5 ml. of methyl alcohol and 10 ml. of anhydrous dioxane and treated, under stirring, with 0.9 ml. of a solution of 0.88 g. of bromine in 10 ml. of chloroform. The reaction mixture, after standing for one hour at room temperature, was poured, with stirring, into 75 ml. of ethyl ether. The resulting crude 14-bromo-4'-epi-6'-hydroxydaunomycin was filtered off and dissolved in a mixture of 5 ml. of acetone and 5 ml. of 0.25 N hydrobromic acid. After 12 hours at room temperature the acid solution was extracted, first with chloroform, in order to remove the aglycones, and then with n-butanol. Several extractions were carried out until all the colored material had passed into the organic phase. After concentration of the combined n-butanol extracts under vacuum, 0.27 g. of the 14-bromo derivative was obtained. This product was dissolved in 10 ml. of water and treated with 0.5 g. of sodium formate.

After 48 hours at room temperature, the reaction mixture was evaporated to a residue under vacuum. The residue, dissolved in 30 ml. of a mixture of chloroform-methanol (2:1 by vol.) was washed with 10 ml. of a 1% aqueous solution of NaHCO$_3$.

The aqueous phase was extracted repeatedly with chloroform until all the colored material had passed into the organic phase. The combined chloroform extracts were dried over anhydrous sodium sulphate, concentrated under reduced pressure to a small volume and treated with one equivalent of 1N hydrochloric acid in anhydrous methanol. By adding 10 volumes of ethyl ether, 0.125 g. of 4'-epi-6'-hydroxyadriamycin (V) in the form of the hydrochloride was obtained.

M.p. 180° C. dec., $[\alpha]_D^{20} = +216°$ ($c = 0.01$ CH$_3$OH). A sample of the product was chromatographed on Kieselgel HF plates (Merck) using as a solvent system: chloroform-methanol-water (130:60:10 by vol.). The R$_f$ of the product was 0.5

BIOLOGICAL ACTIVITY

In vitro studies

1. HeLa cells were exposed to each of compounds (I) and (V) for 2, 8 and 24 hours, after which the compounds were removed and the cells seeded on 5 mm. Falcon plastic dishes (200 cells/plate) in a growth medium. The number of colonies was ascertained microscopically 5 days later.

1. Mouse embryo fibroblasts (MEF) were plated on 35 mm. Falcon plastic dishes, infected 24 hours later with Moloney Sarcoma virus (MSV), and treated for 3 days with different concentrations of the compounds of the invention. The number of foci of transformed cells was microscopically ascertained 5 days after the infection. Uninfected MEF were similarly treated, and at the end of the test, the cells were counted in a hemocytometer. In all the tests, the cells were incubated in a 5% CO$_2$ incubator at 37° C.

The test compounds were dissolved in distilled water and then diluted in culture medium.

The results are reported in Table I as ID$_{50}$ (Inhibiting Dose 50%), calculated on dose-effects lines.

In vivo studies

The antitumor activity of the compounds of the invention was tested on ascites Sarcoma 180. 3 month old CD 1 mice were used. Sarcoma 180 ascites cells were inoculated intraperitoneally (10$^6$ cells/mouse).

The test compounds were dissolved in distilled water, then diluted in Ringer's solution, and administered intraperitoneally 1 day after the tumor implant (10 ml./kg. of body weight). The toxicity of the test compounds was evaluated by macroscopic autoptic examination, mainly in terms of reduction in spleen size. The comparison of the effectiveness of the tested compounds is based on the maximum increase in median survival time, as compared to untreated controls, over the dose range used. The number of Long Term Survivors (LTS) refers to tumor-free mice at the end of the test (60 days).

Results

The activity of the compounds investigated in comparison with the respective parent compounds, daunomycin and adriamycin, on the in vitro systems tested is reported in Table I. Both compounds showed a lower activity than the parent compounds on HeLa cells, on MSV foci and on MEF proliferation. The decrease of activity was higher for the 4'-epi-6'-hydroxydaunomycin, as compared to daunomycin, than for the 4'epi-6'-hydroxyadriamycin, as compared to adriamycin.

The effect observed on ascites Sarcoma 180 is reported in Table II. The optimal antitumor dose (that is the dose at which maximal antitumor effect was found) was 10 mg./kg. for both of the new compounds of the invention.

At the optimal dose, the antitumor activity of the compounds of the invention, as measured by increased life span of the treated mice, as compared to the controls, was lower than that observed after treatment with daunomycin or adriamycin. However, as regards toxicity, it can be seen that the new derivatives according to the invention are considerably less toxic than the parent compounds. This, of course, is a very important and frequently determinant element that must be taken into account when considering a prolonged treatment with high cumulative doses of antitumoral antibiotics.

Table I

In vitro activity of 4'-epi-6'-hydroxydaunomycin and 4'-epi-6'-hydroxyadriamycin. ID$_{50}$(ng./ml.)

| Compound | HeLa cells cloning efficiency | | | MSV foci formation | MEF proliferation |
|---|---|---|---|---|---|
| Time of exposure to drugs (hours) | 2 | 8 | 24 | 72 | 72 |
| Daunomycin[1] | 30 | 13 | 3 | 5.5 | 9 |
| 4'-epi-6'-hydroxy-daunomycin | 1[2] | 1[2] | 1300 | 100 | 250 |
| Adriamycin[1] | 280 | 110 | 18 | 2.5 | 7 |
| 4'-epi-6'-hydroxy-adriamycin | 900 | 1000 | 1000 | 25 | 50 |

[1]average data of a number of tests
[2]inactive at the maximum dose tested (10μg./ml.)

Table II

Activity of 4'-epi-6'-hydroxydaunomycin and 4'-epi-6'-hydroxyadriamycin on ascites Sarcoma 180[1]

| Compound | Dose (mg./kg.) | T/C[3] % | LTS[4] | Toxicity[5] |
|---|---|---|---|---|
| Daunomycin[2] | 0.5 | 146 | 3/20 | |
| | 1 | 172 | 8/55 | |
| | 2 | 192 | 11/68 | |
| | 5 | 176 | | 14/50 |
| | 8 | 78 | | 7/10 |
| 4'-epi-6'-hydroxy-daunomycin | 2 | 100 | | |
| | 10 | 167 | | |
| | 50 | 137 | | 1/10 |
| Adriamycin[2] | 0.5 | 142 | 1/10 | |
| | 1 | 183 | 25/159 | |
| | 2 | 210 | 30/125 | |
| | 5 | 243 | 27/125 | 7/125 |
| | 10 | 212 | 18/139 | 18/139 |
| 4'-epi-6'-hydroxy-adriamycin | 7.5 | 143 | 1/10 | |
| | 10 | 162 | 2/10 | |
| | 15 | 134 | 2/10 | not toxic at dose of 15 mg./kg. |

[1]1 treatment i.p. at day 1
[2]Average data of a number of tests
[3]Median survival time as % over controls
[4]Long Term survivors after 60 days
[5]Number of mice which died as a result of the toxic effects of the compound
Optimal doses are underlined.

Modifications and variations can, of course, be made without departing from the spirit and scope of the invention.

Having thus described our invention, what we desire to secure by Letters Patent and hereby claim is:

1. A compound of the formula

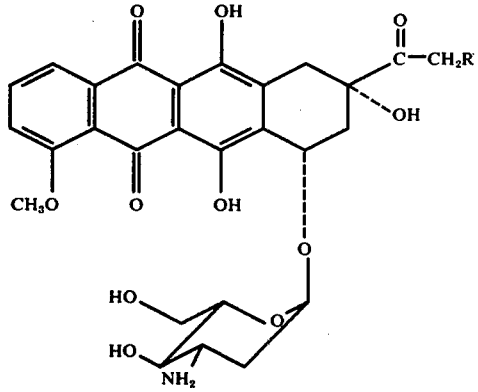

wherein R is H, OH or Br and, in the case where R is H or OH, the hydrochloride salts thereof.

2. A compound according to claim 1, wherein R is H.

3. A compound according to claim 1, wherein R is OH

4. A compound according to claim 1, wherein R is Br.

5. A compound of the formula

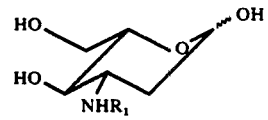

wherein $R_1$ is H or $CF_3CO$.

6. A compound according to claim 5, wherein $R_1$ is H.

7. A compound according to claim 5, wherein $R_1$ is $CF_3CO$.

8. 1,2,3-trideoxy-4,6-di-O-(p-nitrobenzoyl)-3-trifluoroacetamido-L-arabino-hex-1-enepyranose.

9. A process for preparing 1,2,3-trideoxy-4,6-di-O-(p-nitrobenzoyl)-3-trifluoroacetamido-L-arabino-hex-1-enepyranose 10. A method of inhibiting the growth of a tumor selected from the group consisting of Sacroma 180 Ascites and $L_{1210}$ leukemia which comprises intraperitoneally administering to a host afflicted with said tumor an amount of a compound selected from the group consisting of 4'-epi-6'-hydroxydaunomycin and 4'-epi-6'-hydroxyadriamycin sufficient to inhibit the growth of said tumor.

* * * * *

Sheet 1 of 2

UNITED STATES PATENT OFFICE
CERTIFICATE OF CORRECTION

Patent No. 4,025,623  Dated 5/24/77

Inventor(s) Federico Arcamone et al

It is certified that error appears in the above-identified patent and that said Letters Patent are hereby corrected as shown below:

Column 1, line 48: "4-deoxyl;" should read -- (4-deoxy); --; line 49: "(3,4di-O-acetyl)," should read -- (3,4-di-O-acetyl), --.

Column 4, line 9: "The" should read -- This --.

Column 6, line 5: "-α-L-arabion-" should read -- -α-L-arabino- --; line 68: "over a 30 ml. of anhydrous" should read -- over a 30 minute period under stirring and at room temperature to a solution of 3.17 g. of p-nitrobenzoyl chloride in 30 ml. of anhydrous --.

Column 7, lines 16-17: "9.27 $\delta$ (s, 4H aromatic), 9.27 $\delta$ (s, 1H, NH)." should read -- 9.27$\delta$ (s, 1H, NH). --; line 39: "remoed" should read -- removed --; line 48: "$[\alpha]_D^{20}=+388°+5°$" should read -- $[\alpha]_D^{20}=+388°\pm5°$ --.

Column 8, line 32: "1. Mouse" should read -- 2. Mouse --.

Column 9, Table I, line 2 of the heading: "ID$_{50}$ (ng./ml.)" should read -- ID$_{50}$ (mg./ml.) --; Table I, Footnote (2): "10 $\mu$g./ml.)" should read -- (10 mg./ml.) --.

Column 10, line 51: "1-enepyranose" should read -- 1-ene-pyranose comprising reacting 3-amino-2,3-dideoxy-L-arabino-

UNITED STATES PATENT OFFICE
CERTIFICATE OF CORRECTION

Patent No. 4,025,623   Dated 5/24/77

Inventor(s) Federico Arcamone et al

It is certified that error appears in the above-identified patent and that said Letters Patent are hereby corrected as shown below:

hexose with trifluoroacetic anhydride, followed by treatment with a lower aliphatic alcohol, to form 2,3-dideoxy-3-trifluoroacetamido-L-arabinohexose, reacting the latter with p-nitrobenzoyl chloride in pyridine, followed by a mild alkaline hydrolysis. --.

Signed and Sealed this

Eighteenth Day of October 1977

[SEAL]

Attest:

RUTH C. MASON
Attesting Officer

LUTRELLE F. PARKER
Acting Commissioner of Patents and Trademarks